(12) United States Patent
Rath

(10) Patent No.: US 6,686,340 B2
(45) Date of Patent: Feb. 3, 2004

(54) COMPOSITION AND METHOD FOR PREVENTION AND TREATMENT OF HEALTH CONDITIONS CAUSED BY CONSTRICTION OF SMOOTH MUSCLE CELLS

(75) Inventor: Matthias Rath, 4699 Old Ironsides Dr., Cupertino, CA (US) 95054

(73) Assignee: Matthias Rath, Santa Clara, CA (US)

( * ) Notice: Subject to any disclaimer, the term of this patent is extended or adjusted under 35 U.S.C. 154(b) by 0 days.

(21) Appl. No.: 09/885,347

(22) Filed: Jun. 19, 2001

(65) Prior Publication Data

US 2003/0003162 A1 Jan. 2, 2003

(51) Int. Cl.[7] .................. A61K 31/70; A61K 31/59; A61K 31/44; A61K 31/34; A61K 31/195
(52) U.S. Cl. .................. 514/52; 514/168; 514/351; 514/474; 514/561; 514/562; 514/565
(58) Field of Search .................. 514/52, 168, 351, 514/474, 561, 562, 565

(56) References Cited

U.S. PATENT DOCUMENTS

| | | | |
|---|---|---|---|
| 5,198,465 A | | 3/1993 | Diogurdi |
| 5,278,189 A | | 1/1994 | Rath et al. |
| 5,626,883 A | | 5/1997 | Paul |
| 5,650,418 A | | 7/1997 | Rath et al. |
| 5,691,325 A | * | 11/1997 | Sandyk .................. 514/159 |
| 5,891,459 A | | 4/1999 | Cooke et al. |
| 6,207,190 B1 | * | 3/2001 | Richardson et al. ........ 424/472 |

FOREIGN PATENT DOCUMENTS

| | | |
|---|---|---|
| EP | 0891771 | 1/1999 |
| GB | 2029220 | 3/1980 |
| GB | 2268871 | 1/1994 |

OTHER PUBLICATIONS

Bostom A. G.: "The Effect of High Dose Ascorbate Supplementation on Plasma Lipoprote (a) Levels in Patients With Premature Coronary Heart Disease" Pharmacotherapy, vol. 15, No. 4, Jul. 1995, pp. 458–464.

Rath M. et al.: "Nutritional Supplement Program Halts Progression of Early Coronary Atherosclerossis Documented by Ultrafast Computed Tomography" Journal of Applied Nutrition, 1996, 48/3 (68–78).

* cited by examiner

Primary Examiner—Raymond Henley, III
(74) Attorney, Agent, or Firm—Kenyon & Kenyon

(57) ABSTRACT

The invention relates to a method of administering to a human subject a composition comprising a vitamin, an amino acid and a trace element for the prevention and treatment of health conditions caused by constriction of smooth muscle cells in organs of the human body like high blood pressure, asthma, glaucoma and tinnitus. The composition comprises a vitamin such as ascorbic acid, an amino acid such as arginine, and a trace element such as magnesium.

4 Claims, 1 Drawing Sheet

COMPOSITION AND METHOD FOR PREVENTION AND TREATMENT OF HEALTH CONDITIONS CAUSED BY CONSTRICTION OF SMOOTH MUSCLE CELLS

FIELD OF THE INVENTION

The present invention relates generally to the prevention and treatment of health conditions caused by constriction of smooth muscle cells in organs of the human body.

BACKGROUND OF THE INVENTION

The cause of many diseases remains unknown. Among these diseases with unknown origin are most common diseases including high blood pressure, asthma, glaucoma and tinnitus. In case of high blood pressure, one of the most renowned textbooks in medicine, Harrison's Principles of Internal Medicine, states that the cause of the disease is unknown in about 90% of the patients. Worldwide several hundred million people suffer from these health conditions and the economic damage to society from not being able to treat these health conditions effectively is immeasurable.

Worldwide several million people suffer from asthma bronchiale (asthma). In its late stages asthma is a debilitating disease leading to the inability to work and to-social isolation. The cause of this disease remains unknown, even though allergens, genetic disposition and psychological factors have been implicated. The common pathomechanism of this disease is an obstruction of the ventilation channels in the lung (bronchioles) and of the passages to the alveoli where the oxygenation takes place. However, the cellular mechanisms that trigger this obstruction, thereby causing asthma, is not yet understood.

Tinnitus is a form of hearing impairment that in most cases occurs suddenly and without any warning signs. It is estimated that worldwide more than one million patients suffer from tinnitus and related hearing impairment. The origin and the pathogenesis of this disease are unknown and currently there exists no effective therapy to improve the hearing capacity of tinnitus patients. Consequently, many of these patients suffer for years and decades from impaired hearing often with detrimental consequences for the ability to work and their social life.

It is assumed that a variety of apparently different health conditions occurring in different organs is caused by biochemical dysfunction of the same type of cells, called smooth muscle cells. This type of muscle cell is not susceptible to conscious control as opposed for example to the muscles of the arms or legs. Proper metabolic function of smooth muscle cells would, therefore, be a key to avoiding health problems in all those organs where smooth muscle cells play a critical functional role.

In case of asthma it is assumed that the common cellular mechanism could be found. The walls of bronchioles and alveoli channels contain a layer of smooth muscle cells, If these cells would constrict—irrespective of the trigger—the diameter of these lung ducts would decrease, leading to a decrease in ventilation and oxygenation. Thus, the typical symptoms of a patient with asthma and/or obstructive lung disease would occur.

In case of tinnitus and hearing impairment it is conceivable that the hearing impairment is caused by spasm of smooth muscle cells which form the lining of blood vessels responsible for blood supply to the inner ear and to the nerve cells mediating acoustic signals. It was further assumed that the spasm of these smooth muscle cells in the ear capillaries is caused by a lack of co-enzymes and other bioenergy molecules essential for optimum metabolic function of these cells.

There was not found any earlier description of this concept in the scientific literature.

Recent progress has been made in understanding the metabolism of cells and the role of certain biochemical compounds in maintaining their proper function. Consequently, correcting the dysfunction of smooth muscle cell metabolism would be a key to preventing and treating a variety of health conditions in different organs.

It was further found that the cellular dysfunction could be caused by a deficiency of certain biochemical compounds needed as co-enzymes in the tricarbon acid-cycle, the so-called Krebs-cycle, the respiration chain and for other metabolic functions in smooth muscle cells. The health conditions that can potentially be prevented and treated include, but are not limited thereto, the following organs and diseases:

Blood vessels, lungs, eye, uro-genital tract, gastro-intestinal tract

High blood pressure, angina pectoris, tinnitus, impotence, asthma and other forms of obstructive lung diseases, glaucoma and other forms of increased eye pressure, premenstrual syndrome, infertility, spasms of the ureter, urethra, singultus, stomach cramps, and spasms of the gall duct.

OBJECTS AND SUMMARY OF THE INVENTION

It is therefore an object of this invention to administer a composition of biochemical substances to a patient suffering from health conditions as mentioned above but not limited thereto which comprises compounds of various vitamins, various amino acids and various trace elements.

It is a further object of this invention to administer to a patient compositions of biochemical substances consisting of at least one ascorbate compound selected from the group consisting of ascorbic acid, pharmaceutically acceptable ascorbate salts and/or mixtures thereof.

It is another object of this invention to administer a composition of biochemical substances to a patient consisting of one ascorbate compound with at least one arginine compound selected from the group of arginine hydrochlorides, pharmaceutically acceptable arginine salts and/or mixtures thereof.

It is a further object of this invention to administer to a patient a composition of biochemical substances consisting of ascorbate compounds, arginine compounds and at least one magnesium compound selected from magnesium or pharmaceutically acceptable magnesium salts and/or mixtures thereof.

It is a further object of this invention to administer to a patient the therapeutical composition of biochemical substances like Ascorbic Acid, Ascorbyl Palmitate, Beta-, Gamma-, Delta-Tocopherol-Mix, Beta-Carotene, Biotin, Calcium Ascorbate, Calcium Citrate, Calcium Glycinate, Carotinoid-Mix: (Alpha-Carot., Lutein. Zea-, Kryptoxanthin), Cholecalciferol, Chromium Glycinate, Citrus Bioflavonoids, Coenzyme Q10, Copper Glycinate, Cyanocobalamin, d-Alpha-Tocopherol, d-Calcium Pantothenate, Di-calcium Phosphate, Folic Acid, Inositol, L-Arginine, L-Carnitine, L-Cysteine, L-Lysine, L-Proline, L-Selenomethionine, Magnesium Ascorbate, Magnesium Citrate, Magnesim Glycinate, Manganese Chelate, Molybdenum Glycinate, Niacin, Niacinamid, Potassium Chelate, Pycnogenol, Pyrodoxine, Riboflavin, Thiamine, Zinc Glycinate. It is understood that a skill in the art would readily determine the dosage of these added components.

It is a further object of this invention to administer to a patient a composition of biochemical substances whereas these formulas are provided to a patient in form of tablets, pills, injections, infusions, inhalations, suppositories or other pharmaceutically acceptable carriers and/or means of delivery.

Figure 1:
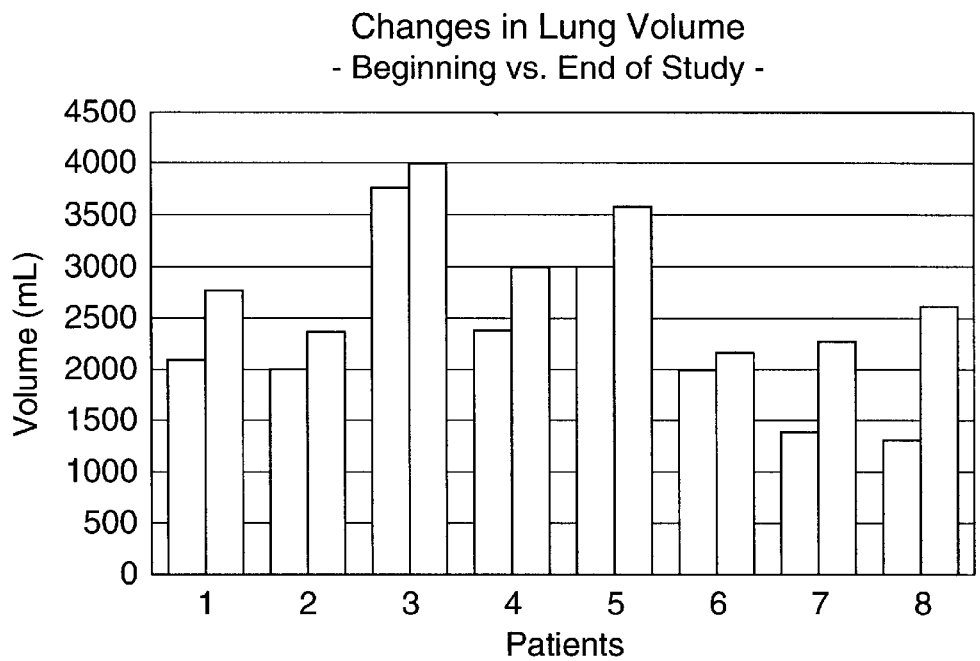
FIG. 1 depicts the changes in lung volume—beginning vs end of study.

This concept was clinically tested for several of the above-mentioned health conditions, i.e. high blood pressure, asthma and tinnitus.

The treatment with such compositions of biochemical substances leads to at least partly considerable relaxations of smooth muscle cells resulting in the increase of artery diameter of large arteries (e.g. aorta) lowering elevated blood pressure, increasing artery diameter of midsize arteries (e.g. coronary arteries) resulting in a decrease of angina pectoris, resulting in the increase of diameter of arterioles and capillaries (e.g. arteries of the ear) leading to improved hearing, relaxation of smooth muscle cells in lung bronchioles and alveoli leading to an increase of airway diameter following a decrease of asthma symptoms, the relaxation of canal systems of the eye resulting in an increase of diameter e.g. of tear ducts decreasing eye pressure leading to a decreased risk of glaucoma and blindness, the relaxation of smooth muscle cells in ovarian tubes and uterus resulting in relaxation of muscle tissue improving fertility and decreasing PMS symptoms, relaxation of smooth muscle cells in gall ducts, ureter and urethra increasing the diameter of ducts resulting in a decreased risk of cramps caused by gall stones or kidney stones.

Having disclosed a preferred embodiment of the present invention, the following examples are provided by way of illustration only and are not limiting the invention in any way.

EXAMPLE

Compositions of biochemical substances as listed below have been administered patients in the daily amounts of units of the substances shown in this example

| Biochemical Substances | Units | Amount |
| --- | --- | --- |
| Ascorbic Acid | mg | 680 |
| Ascorbyl Palmitate | mg | 620 |
| Beta-, Gamma-, Delta-Tocopherol-Mix | mg | 22 |
| Beta-Carotene | I.U. | 1665 |
| Biotin | mcg | 65 |
| Calcium Ascorbate | mg | 1050 |
| Calcium Citrate | mg | 200 |
| Calcium Glycinate | mg | 35 |
| Carotinoid-Mix: (Alpha-Carot., Lutein, Zea-, Kryptoxanthin) | mcg | 50 |
| Cholecalciferol | I.U. | 130 |
| Chromium Glycinate | mcg | 10 |
| Citrus Bioflavonoids | mg | 650 |

-continued

| Biochemical Substances | Units | Amount |
| --- | --- | --- |
| Coenzyme Q10 | mg | 7 |
| Copper Glycinate | mcg | 330 |
| Cyanocobalamin | mcg | 20 |
| d-Alpha-Tocopherol | I.U. | 230 |
| d-Calcium Pantothenate | mg | 40 |
| Dicalcium Phosphate | mg | 15 |
| Folic Acid | mcg | 90 |
| Inositol | mg | 35 |
| L-Arginine | mg | 790 |
| L-Carnitine | mg | 35 |
| L-Cysteine | mg | 35 |
| L-Lysine | mg | 110 |
| L-Proline | mg | 110 |
| L-Selenomethionine | mcg | 20 |
| Magnesium Ascorbate | mg | 1050 |
| Magnesium Citrate | mg | 400 |
| Magnesim Glycinate | mg | 40 |
| Manganese Chelate | mcg | 1300 |
| Molybdenum Glycinate | mcg | 4 |
| Niacin | mg | 10 |
| Niacinamide | mg | 35 |
| Potassium Chelate | mg | 20 |
| Pycnogenol | mg | 7 |
| Pyrodoxine | mg | 10 |
| Riboflavin | mg | 7 |
| Thiamine | mg | 7 |
| Zinc Glycinate | mg | 7 | mg = milligrams,
mcg = micrograms,
I.U. = International Units

However, a composition of biochemical substances according to the above example may be varied with individual components, others than of the formula used and irrespective of their amounts which are more than 80% identical with such substances. Further the amounts of individual ingredients provided per day may be not less than 10% and not more than 1000% of the amounts as shown in the example.

The concept of this invention was tested in a prospective clinical study with eight asthma patients. These patients received the biomedical compounds listed above as a daily dosage for a period of four months. At the beginning and at the end of the study the lung volume was measured in each patient. During the study the asthma patients increased their lung volume in average by more than 20%. The most significant result of this study was the fact that the percentage of lung volume increase was much higher for those patients with the lowest base line values with indicates that this therapy is particularly valuable with patients with sever asthma and a severe breathing impairment as shown in FIG. 1.

Figure 2:
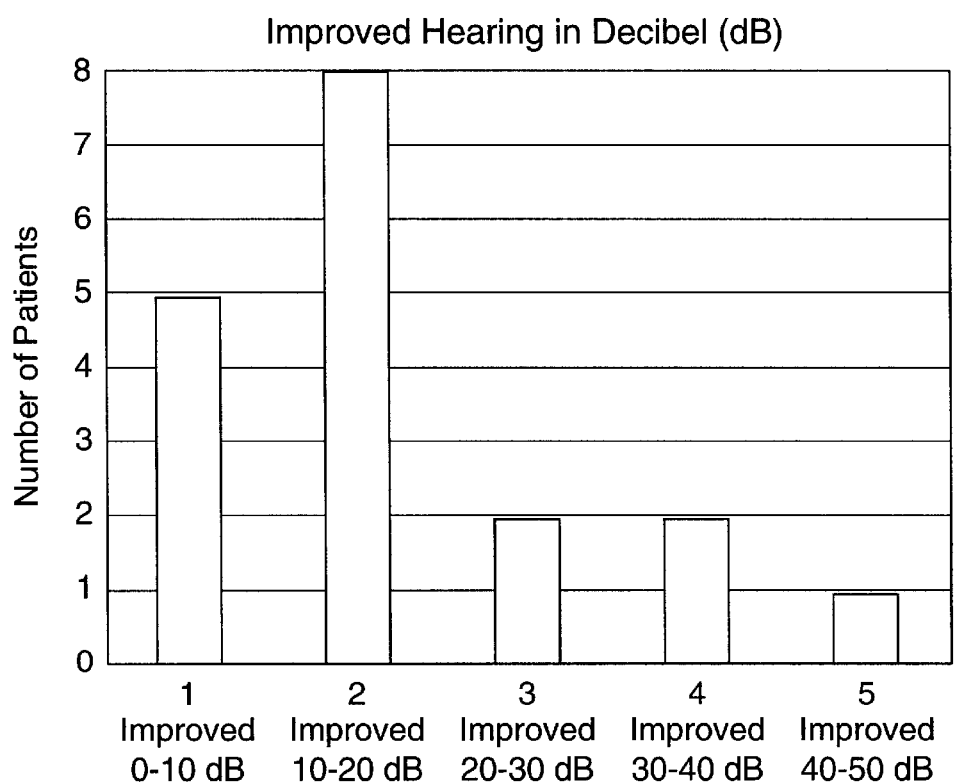
FIG. 2 depicts the improved hearing in decibel (db).

The concept of this invention was tested in a prospective clinical study with 18 tinnitus patients for a period of four months. The hearing capacity was objectively documented by audiometry. The before/after results of the audiometry measurements are shown in FIG. 2.

Five patients had little or no improvement of their hearing capacity (0–10 decibel [dB]), eight patients had improvements between 10 and 20 dB, two patients between 20 and 30 dB, two patients between 30 and 40 dB and for one patient an improvement of hearing capacity between 40 and 50 dB was documented.

By now it is apparent that the administering of the compositions to patients being endangered of suffering or suffering from health conditions caused at least in part by constriction of smooth muscle cells in organs of their body. Although preferred embodiments and examples have been disclosed it is understood that the invention is in no way limited thereby but rather is defined by the claims that follow and the equivalents thereof.

What is claimed is:

1. A method of preventing or treating a health condition caused by constriction of smooth muscle cells in organs of human comprises administering to said human a composition comprising ascorbic acid, ascorbyl palmitate, beta-, gamma, delta-tocopherol-mix, beta-carotene, biotin, calcium ascorbate, calcium citrate, calcium glycinate, carotinoid-mix, cholecalciferol, chromium glycinate, citrus bioflavonoids, coenzyme Q10, copper glycinate, cyanocobalamin, d-alpha-tocopherol, d-calcium pantothenate, dicalcium phosphate, folic acid, inositol, L-arginine, L-carnitine, L-cysteine, L-lysine, L-proline, L-selenomethionine, magnesium ascorbate, magnesium citrate, magnesium glycinate, manganese chelate, molybdenum glycinate, niacin, niacinamide, potassium chelate, pycnogenol, pyrodoxine, riboflavin, thiamine, and zinc glycinate.

2. A method of preventing or treating a health condition caused by constriction of smooth muscle cells in organs of a human comprises administering to said human a composition comprising 680 mg ascorbic acid, 620 mg ascorbyl palmitate, 22 mg beta-, gamma-, delta-tocopherol-mix, 1665 I.U. beta-carotene, 65 μg biotin, 1050 mg calcium ascorbate, 200 mg calcium citrate, 35 mg calcium, glycinate, 50 μg, carotinoid-mix 130 I.U. cholecalciferol, 10 μg chromium glycinate, 650 mg citrus bioflavonoids, 7 mg coenzyme Q10, 330 μg copper glycinate, 20 μg cyanocobalamin, 230 I.U. d-alpha-tocopherol, 40 mg d-calcium pantothenate, 15 mg dicalcium phosphate, 90 μg folic acid, 35 mg inositol, 790 mg L-arginine, 35 mg L-carnitine, 35 mg L-cysteine, 110 mg L-lysine, 110 mg L-proline, 20 μg L-selenomethionine, 1050 mg magnesium ascorbate, 400 mg magnesium citrate, 40 mg magnesium glycinate, 1300 μg manganese chelate, 4 μg molybdenum glycinate, 10 mg niacin, 35 mg niacinamide, 20 mg potassium chelate, 7 mg pycnogenol, 10 mg pyrodoxine, 7 mg riboflavin, 7 mg thiamine, and 7 mg zinc glycinate.

3. A method as in one of claims 1–2 in which the composition is provided in the form of a tablet, a pill, an injection, an infusion, an inhalation, or a suppository.

4. A method as in one of claims 1–2 in which the composition is provided in pharmaceutically accepted carriers and means of delivery.

* * * * *